United States Patent
Ogino et al.

(10) Patent No.: US 6,252,054 B1
(45) Date of Patent: Jun. 26, 2001

(54) IMMOBILIZATION OF SH GROUP-CONTAINING COMPOUNDS IN THE PRESENCE OF A SULFITE-CONTAINING ANTIOXIDANT

(75) Inventors: Eiji Ogino, Kobe; Takehiro Nishimoto, Osaka; Michio Nomura, Kakogawa, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/444,305

(22) Filed: Nov. 22, 1999

(30) Foreign Application Priority Data

Nov. 20, 1998 (JP) .................................................. 10-330578

(51) Int. Cl.⁷ .......................... C07K 17/02; C07K 17/14; C12N 11/16; G01N 33/551; G01N 33/544
(52) U.S. Cl. .......................... 530/402; 435/176; 435/177; 435/178; 435/179; 435/180; 435/188; 436/524; 436/528; 436/529; 436/530; 436/531; 530/811; 530/812; 530/813; 530/814; 530/815
(58) Field of Search .................... 435/174, 176, 435/177, 178, 179, 180, 188; 530/402, 811, 812, 813, 814, 815; 436/524, 528, 529, 530, 531

(56) References Cited

U.S. PATENT DOCUMENTS

| | | | |
|---|---|---|---|
| 4,247,642 | * | 1/1981 | Hirohara et al. ...................... 435/178 |
| 5,108,916 | * | 4/1992 | Cobbs et al. .......................... 435/135 |
| 5,298,406 | * | 3/1994 | Loyd et al. ............................. 435/17 |
| 5,824,522 | * | 10/1998 | Ikenaka et al. ....................... 435/106 |
| 5,866,387 | * | 2/1999 | Ogiho et al. .......................... 435/179 |
| 5,874,569 | * | 2/1999 | Elsner et al. ............................ 536/51 |

OTHER PUBLICATIONS

Tanaka et al, Modern Chemistry, Jul. 1992, pp. 24–30.

* cited by examiner

*Primary Examiner*—David M. Naff
(74) *Attorney, Agent, or Firm*—Connolly, Bove, Lodge & Hutz, LLP.

(57) ABSTRACT

Immobilization of SH group-containing compounds on a solvent-insoluble support is carried out in the presence of an antioxidant to prevent oxidation of SH groups to S—S bonds. This improves immobilization efficiency and suppresses deterioration of inherent characteristics of the SH group-containing compound. Antioxidants include sodium pyrosulfite (sodium disulfite), sodium sulfite, sodium hydrogensulfite, sodium hydrosulfite and L-ascorbic acid. SH group-containing compounds include cysteine, peptides or proteins containing cysteine and thiol compounds such as ethanethiol, aminoethanethiol, benzylthiol and thiophenol. Preferably, the SH group-containing compound has a molecular weight not more than $3 \times 10^4$. The support may be activated by a functional group such as glycidyl, imidocarbonato, tosyl, tresyl, carboxyl, amino, azido or hydroxyl. The support can be inorganic such as glass beads or organic such as a synthetic polymer or a polysaccharide.

8 Claims, 1 Drawing Sheet

SEQUENCE LISTING

<160> NUMBER OF SEQ ID NOS: 2

<210> SEQ ID NO 1
<211> LENGTH: 58
<212> TYPE: PRT
<213> ORGANISM: Artificial Sequence
<220> FEATURE:
<223> OTHER INFORMATION: MP47C peptide

<400> SEQUENCE: 1

Met Thr Thr Tyr Lys Leu Val Ile Asn Gly Lys Thr Leu Lys Gly Glu
1               5                   10                  15

Thr Thr Thr Lys Ala Val Asp Ala Glu Thr Ala Glu Lys Ala Phe Lys
            20                  25                  30

Gln Tyr Ala Asn Asp Asn Gly Val Asp Gly Val Trp Thr Tyr Asp Pro

```
                    35                  40                  45
Ala Thr Lys Thr Phe Thr Val Thr Glu Cys
        50                  55

<210> SEQ ID NO 2
<211> LENGTH: 184
<212> TYPE: DNA
<213> ORGANISM: Artificial Sequence
<220> FEATURE:
<223> OTHER INFORMATION: DNA coding for MP47C peptide

<400> SEQUENCE: 2 cat atg acc acc tat aaa ctg gtt atc aac ggt aaa acc ctg aaa ggt        48
    Met Thr Thr Tyr Lys Leu Val Ile Asn Gly Lys Thr Leu Lys Gly
    1               5                   10                  15 gaa acc acc acc aag gct gtt gac gct gaa acc gct gaa aaa gca ttt        96
Glu Thr Thr Thr Lys Ala Val Asp Ala Glu Thr Ala Glu Lys Ala Phe
                20                  25                  30 aaa cag tat gct aac gac aac ggt gtc gac ggt gtt tgg acc tat gac       144
Lys Gln Tyr Ala Asn Asp Asn Gly Val Asp Gly Val Trp Thr Tyr Asp
                35                  40                  45 ccc gct acc aaa acc ttt acc gtt acc gaa tgc taagctt                   184
Pro Ala Thr Lys Thr Phe Thr Val Thr Glu Cys
        50                  55
```

IMMOBILIZATION OF SH GROUP-CONTAINING COMPOUNDS IN THE PRESENCE OF A SULFITE-CONTAINING ANTIOXIDANT

TECHNICAL FIELD

The present invention relates to a method for immobilizing an SH (sulfhydryl) group-containing compound on a solvent-insoluble support.

BACKGROUND ART

As a method for immobilizing a compound on a solvent-insoluble support for use as a ligand for specific adsorption, many investigations have been undertaken in the diverse field of immobilized enzymes, affinity chromatography, ion exchange chromatography, etc. and some methods are used on the industrial application.

As a representative method for immobilization known in the field of immobilized enzymes, there can be mentioned: (1) the method which comprises forming the imidocarbonate on the support by the cyanogen bromide activating method and, then, causing it to react with the amino group of the compound to serve as a ligand; (2) the so-called acid azide derivative method which comprises, sequentially, esterification of the carboxyl group on a support, hydrazide formation, conversion to the azide and substitution thereof with the amino group of the compound to serve as a ligand; (3) the so-called diazo method which comprises forming a diazonium salt on a support and letting it react with the amino group of the compound to serve as a ligand; (4) the so-called condensation reagent method which comprises condensing the amino or carboxyl group on a support with the carboxyl or amino group of the compound to serve as a ligand in the presence of a condensing agent; (5) the so-called alkylation method which comprises modifying a support with bromoacetyl or 4,6-dichloro-s-triazinyl and causing the resulting derivative to react with the amino group of the compound to serve as a ligand; and (6) the so-called matrix-crosslinking method which comprises crosslinking the amino group on a support and the amino group of the compound to serve as a ligand with glutaraldehyde followed by reduction (Atsuo Tanaka & Takuo Kawamoto: Modern Chemistry, 24 to 30, July 1992).

However, those methods have the drawbacks, namely (a) when the compound to serve as a ligand contains an SH group, the efficiency of immobilization is relatively low; and (b) when the compound to serve as a ligand is an SH group-containing peptide or protein, in particular, the inherent activity of the compound (enzyme activity, binding activity, etc.) is sometimes sacrificed.

The inventors of the present invention discovered that when a peptide or protein to serve as a ligand contains an SH group, the above-mentioned phenomena (a) and (b) occur during its immobilization on a solvent-insoluble support. Similar phenomena are also observed with compounds other than peptides and proteins provided that they contain SH groups. There is no information in the available literature to the effect that the above phenomena occur when a compound to serve as a ligand is immobilized on an inert support.

SUMMARY OF THE INVENTION

In the above state of the art, the present invention has its objects to provide a method for immobilization which is capable of improving the efficiency of immobilization in the reaction between an SH group-containing compound and a solvent-insoluble support as well as suppressing the deterioration of the inherent characteristic of the SH group-containing compound due to immobilization.

For accomplishing the above object, the inventors of the present invention did an extensive investigation concerning various conditions of the reaction and endeavored to establish a method for immobilization which is capable of improving the efficiency of immobilization and suppressing the deterioration of the inherent characteristics of SH group-containing compounds. As a result, the inventors discovered the involvement of SH group, as a major factor, in the above-mentioned phenomena (a) and (b). Moreover, in view of the fact that those phenomena are liable to occur in reactions conducted in aqueous solution in the high pH (>7) region, the inventors assumed that, under the conditions of immobilization reactions, SH groups are oxidized, for instance, to give the S—S bond.

The S—S bond may at times be formed within the molecule of the compound to serve as a ligand or may also occur between the molecules. It can be thought that when the reaction site (functional group) necessary to be utilized for immobilization of the compound to serve as a ligand is SH group, the formation of the S—S bond inactivates the reaction site and that, when the reaction site is a functional group other than SH group, the reaction site is hidden in the interior of the molecule as the S—S bond is formed. It can be thought that the decrease in immobilization efficiency occurs probably in such situations. Moreover, it can also be assumed that the formation of the S—S bond causes the deterioration of the inherent characteristic of the SH group-containing compound.

Based on the above experience and assumption, the inventors paid attention to the importance of avoiding formation of the S—S bond and, after many investigations, found that the above-mentioned object can be accomplished by conducting the reaction between a solvent-insoluble support and an SH group-containing compound in the presence of an antioxidant. The present invention has been developed on the basis of the above finding.

The present invention, therefore, is directed to a method for immobilizing an SH group-containing compound which comprises reacting a solvent-insoluble support with the above-mentioned compound in the presence of an antioxidant.

DETAILED DESCRIPTION OF THE INVENTION

Figure 1:
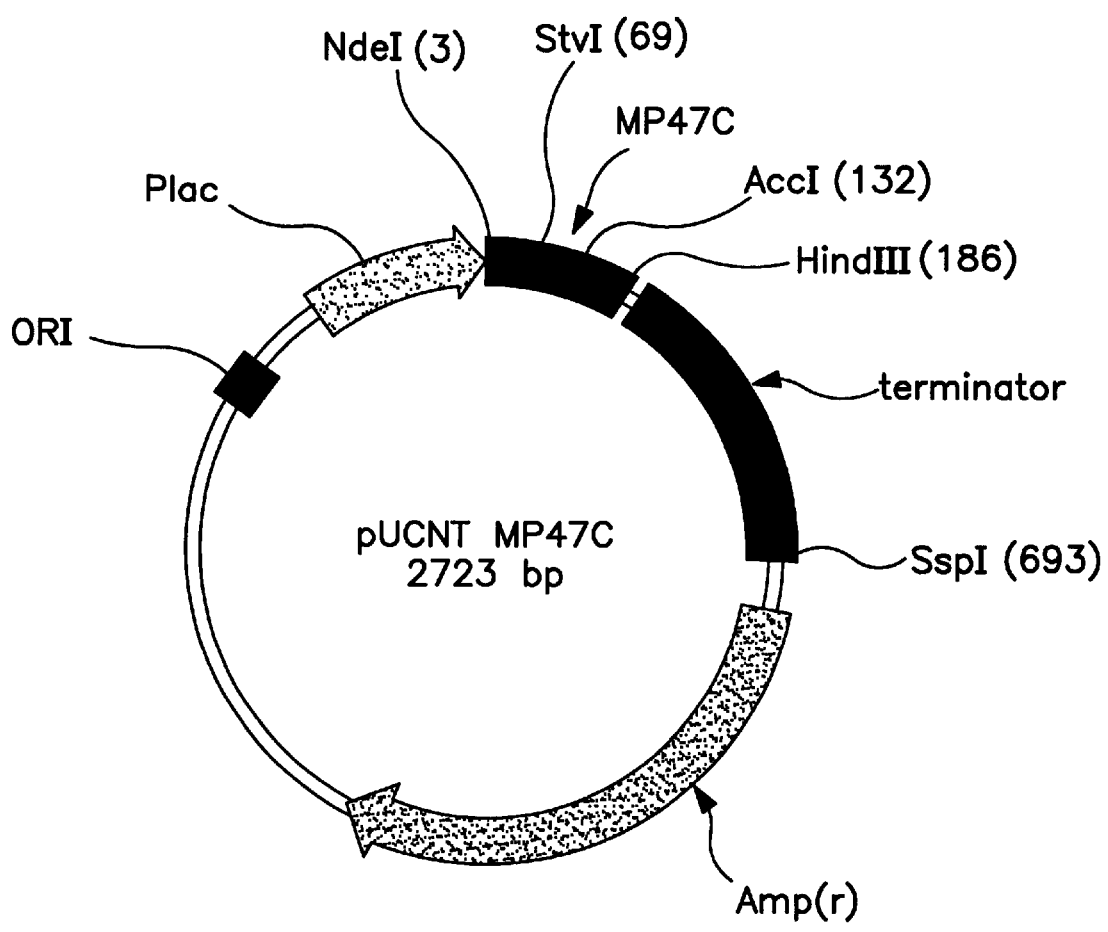
FIG. 1 shows a pUCNT MP47C vector.

The present invention is now described in detail.

According to the present invention, the solvent-insoluble support means a support which is not soluble in a solvent to be employed. In the preferred embodiment of the present invention, the solvent-insoluble support is a solvent-insoluble support in case of using water as the solvent, that is to say a water-insoluble support.

The water-insoluble support mentioned above is not particularly restricted but includes inorganic supports such as glass beads, silica gel, etc.; organic supports such as synthetic polymers, e.g. crosslinked polyvinyl alcohol, crosslinked polyacrylate, crosslinked polyacrylamide, crosslinked polystyrene, etc. and polysaccharides, e.g. crystalline cellulose, crosslinked cellulose, crosslinked agarose, crosslinked dextran, etc.; and organic-organic, organic-inorganic or other complex supports as obtained by using said support materials in combination.

Furthermore, when an SH group-containing compound immobilized on a solvent-insoluble support is to be used in chromatography or as an adsorbent, the solvent-insoluble support is preferably a hydrophilic support. This is because a hydrophilic support is comparatively low in nonspecific adsorption and satisfactory to adsorption specificity caused by ligand (immobilized SH group-containing compound). The hydrophilic support in this specification means a support which shows a contact angle of not greater than 60° with respect to water when the compound constituting the support is tested in a board form.

The hydrophilic support mentioned above is not particularly restricted but includes, for example, supports which comprise various polysaccharides and derivatives thereof, such as cellulose, acetylcellulose, chitosan, chitin, agarose, dextran, etc.; and such other supports as polyvinyl alcohol, co(ethylene-vinyl acetate) polymer hydrolyzate, polyacrylamide, polyacrylic acid, polymethacrylic acid, poly(methyl methacrylate), polyacrylic acid-polyethylene graft, polyacrylamide-polyethylene graft, and glass, among others.

Among those hydrophilic supports, hydroxyl group-containing supports are preferred in adsorption affinity and selectivity. Particularly when the support immobilized on an SH group-containing compound is used as an adsorbent, a porous cellulosic gel is one of the most suitable kinds of supports because it has the following beneficial characteristics; thus, (1) Because such gels are comparatively high in mechanical strength and tough, they are not disintegrated or give dusts in stirring and other mechanical procedures and when they are packed into columns, no compaction or plugging occurs even when a fluid is passed at a high flow rate, thus permitting operations at high flow rates. Moreover, its pore structures are not easily altered by autoclaving, for instance.

(2) Composed of cellulose, those gels are hydrophilic and contain many hydroxyl groups available for ligand binding and, moreover, they are relatively low in nonspecific adsorption.

(3) Because those gels are comparatively high in strength even when the void volume is increased, large adsorption capacities fully comparable to those of soft gels can be obtained.

The cellulosic gel in this specification means any cellulose derivative the backbone chain of which is composed of cellulose, such as cellulose or acetylcellulose. However, the present invention is not restricted to the use of such gels.

The SH group-containing compound according to the present invention means a compound to be immobilized on a solvent-insoluble support and having one or more —SH (sulfhydryl) group within its molecule. The SH group in such a compound may assume an ionized form, e.g. —S$^-$Na$^+$, —S$^-$K$^+$, depending on the kind of solution in which it occurs, or may be added in the form of a salt, e.g. —SNa or —SK, at the time of reaction. However, since these forms are essentially the same, the term SH group is used herein in the generic sense, including the above cases.

The SH group-containing compound mentioned above is not particularly restricted but includes, for example, cysteine, peptides or proteins containing cysteine as a constituent amino acid and thiol compounds (high, medium or low molecular compounds having SH group in the backbone chain or in side chains, inclusive of ethanethiol, aminoethanethiol, benzylthiol, thiophenol and compounds having such moieties in side chains or termini). The SH group-containing compound mentioned above is preferably at least one member selected from the group consisting of amino acid, peptide and protein.

The molecular weight of said SH group-containing compound was a subject of our intensive study. The study revealed that as the molecular weight is increased, the effect of the invention is detracted. Thus, as far as SH group-containing compounds having molecular weights up to $3 \times 10^4$ are concerned, a significant difference was found in the effect of the invention according to whether an antioxidant is added or not. On the other hand, for proteins which are high polymers having molecular weights of the order of $1.5 \times 10^5$, the difference in the effect of the invention was relatively small. Therefore, the molecular weight of said SH group-containing compound is preferably not greater than $3 \times 10^4$.

The antioxidant according to the present invention means a substance which has the property to prevent or suppress oxidation of a compound in a reaction system and includes, for example, a substance which either directly inhibits oxidation of a compound or becomes oxidized to thereby inhibit oxidation of a compound in a reaction system and a substance having the property to purge dissolved oxygen from the reaction system. Of course, a similar effect may be achieved by decreasing dissolved oxygen substantially through degassing or cooling of the reaction solvent but in consideration of workability and universality of application, addition of an antioxidant is a better choice leading to a better outcome more effectively and safely.

The antioxidant mentioned above includes a large variety of substances, among them, also includes SH group-containing compounds. Mercaptoethanol is a representative example. However, when the immobilization reaction proceeds as the solvent-insoluble support is subject to nucleophilic reaction as it is the case with a support having glycidyl (epoxy) groups, the antioxidant mercaptoethanol itself may react and be immobilized. When such cases are taken into consideration, the use of an antioxidant having nucleophilicity is subject to limitation in terms of the scope of application. Of course, although even such an antioxidant is sufficiently useful for certain reactions, a widely useful antioxidant which can be used without such fear is preferred.

In the present invention, said antioxidant is preferably at least one member selected from the group consisting of sodium pyrosulfite (sodium disuflite), sodium sulfite, sodium hydrogensulfite, sodium hydrosulfite and L-ascorbic acid. Those antioxidants are advantageous in that they can be utilized in the immobilization reaction of a large majority of SH group-containing compounds with a solvent-insoluble support.

In the present invention, the molar concentration ratio of the antioxidant to the SH group-containing compound is preferably 1000:1 to 1:1000. Outside of this range, the concentration of the antioxidant is preferably 1 $\mu$mol/L to 1 mol/L. It is more preferable that both conditions be satisfied. In such cases, the antioxidant expresses its antioxidant activity sufficiently to maximize the immobilization rate of the SH group-containing compound and the activity retention thereof after immobilization. It should be noted that the molar concentration mentioned above is the molar concentration in a reaction system.

In reacting the solvent-insoluble support with the SH group-containing compound according to the method for immobilization of the present invention, the efficiency of immobilization can be improved by activating the solvent-insoluble support somehow in advance.

In the preferred embodiment of the present invention, the solvent-insoluble support is a support activated with at least one kind of functional group selected from the group consisting of glycidyl (epoxy), imidocarbonate, tosyl, tresyl, carboxyl, amino, azido and hydroxyl. When the reaction of the support with an SH group-containing compound is curried out in the presence of an antioxidant, not only the immobilization rate of the SH group-containing compound but also the activity retention rate thereof after immobilization is high, therefore the use of such an activated solvent-insoluble support is effective.

BEST MODE FOR CARRYING OUT THE INVENTION

The following examples are merely intended to illustrate the present invention in further detail and should by no means be construed as defining the scope of the invention.

EXAMPLE 1

Immobilization of Aminoethanethiol on Sephacryl S1000 (Sephacryl-AET-a)

(1) Epoxy-activation of Sephacryl S1000

To 83 ml of Sephacryl S1000 (Amersham Pharmacia Biotech) was added a sufficient amount of water to make 186 ml, and 113 ml of 2 M sodium hydroxide-water was further added. The temperature was then adjusted to 40° C. To this mixture was added 38 ml of epichlorohydrin (Wako Pure Chemical Ind.), and the reaction was carried out at 40° C. for 2 hours. After completion of the reaction, the reaction mixture was thoroughly washed with water on a glass filter to provide epoxy-activated Sephacryl S1000.

(2) Immobilization of aminoethanethiol and quantitation of immobilized aminoethanethiol In 15 ml of 0.05 M borate buffer (pH 10.0) were dissolved 1.20 mg of 2-aminoethanethiol (Wako Pure Chemical Ind.) and 150 mg of sodium sulfite (Wako Pure Chemical Ind.), and the solution was readjusted to pH 10 with 0.01 N sodium hydroxide-water and made up to 25 ml. To 5 ml of the above epoxy-activated Sephacryl S1000 was added the above aminoethanethiol solution (whole amount), and after 18 hours of shaking at 37° C., the mixture (aminoethanethiol:sodium sulfite=1:76, sodium sulfite=47.6 mmol/L) was washed with a sufficient amount of physiological saline on a glass filter to provide Sephacryl-AET-a (0.20 mg/ml-gel). The amount of immobilized aminoethanethiol was determined by the TNBS (trinitrobenzenesulfonic acid) colorimetric assay of amino groups using the supernatants before and after the reaction.

EXAMPLE 2

Immobilization of Cysteine on Tresyl-Toyopearl (Toyopearl-Cys-a) and Quantitation of Immobilized Cysteine In 4 ml of a coupling buffer (pH 8.2, 0.5 M sodium chloride-0.1 M carbonate buffer) were dissolved 0.50 mg of L-cysteine hydrochloride monohydrate (Wako Pure Chemical Ind.) and 1.0 mg of sodium pyrosulfite (Wako Pure Chemical Ind.). Then, 800 mg of AF-tresyl-Toyopearl 650 was added in dry state and the reaction was conducted at room temperature overnight.

The reaction mixture was washed with 0.5 M sodium chloride-water, then a block buffer (pH 8.0, 0.5 M sodium chloride-0.1 M Tris-HCl buffer) was added, and the reaction was carried out at room temperature for 2 hours (cysteine:sodium pyrosulfite=1:1.89, sodium pyrosulfite=1.3 mmol/L). This reaction mixture was further washed with 0.5 M sodium chloride-water to provide Toyopearl-Cys-a (0.11 mg/ml-gel). The amount of immobilized cysteine was determined by said amino group assay as in Example 1.

EXAMPLE 3

Immobilization of an IgG-binding Peptide (MP47C on a Porous Support (Kac) Using Sodium Hydrosulfite (Kac-MP47C-a) and the Evaluation of IgG-binding Activity (1) Production of MP47C peptide To acquire MP47C peptide shown in the sequence listing under SEQ ID NO:1, a DNA coding for MP47C peptide was designed as shown in the sequence listing under SEQ ID NO:2 and synthesized so that it could be ligated to the pUCNT vector [Japanese Kokai Publication Hei-4-212692] utilizing Nde I and Hind III restriction enzyme sites for the 5'-end and 3'-end, respectively.

The DNA having the above sequence was ligated to the pUNT vector after cleavage with the restriction enzymes Nde I and Hind III (Takara Shuzo) using DNA Ligation Kit Ver. 2 (Takara Shuzo) according to the protocol to construct a pUCNT MP47C vector (FIG. 1).

Using the routine technique, this pUCNT MP47C vector DNA was introduced into *Escherichia coli* HB101 (Funakoshi Hanbai) and a transformant was selected by using resistance to the antibiotic ampicillin as a marker.

From this transformant, the plasmid DNA was extracted and the gene sequence was analyzed in the routine manner to confirm that this pUCNT MP47C vector had the designed DNA sequence. Then, this transformant was shake-cultured in 6 L of L-broth (5 g/L NaCl, 10 g/L bactotrypsin, 5 g/L yeast extract) at 37° C. for 20 hours and the cells were harvested by centrifugation (Hitachi RPR9-2 rotor, 4° C., 6000 rpm., 20 min). The pellet obtained was suspended in 300 ml of TE buffer (20 mM Tris-HCl, 1 mM EDTA; pH 7.5) and sonicated (BRANSON 250, 6 min.×3, on ice) and the supernatant was recovered by centrifugation (Hitachi RPR16 rotor, 4° C., 15000 rpm, 20 min). The supernatant thus recovered was heat-treated at 70° C. for 10 minutes, then centrifuged again (Hitachi RPR16 rotor, 4° C., 15000 rpm, 20 min) to recover 300 ml of a supernatant. The supernatant was purified by high performance liquid chromatography (column: Waters $\mu$ BONDASPHERE $5\mu$ C18 300A, 19.0×150 mm). Thus, the column was first activated by passing 40 ml of acetonitrile at a flow rate of 5 ml/min and, then, 300 ml of a sample was passed at the same flow rate. The column was then washed with 200 ml of 0.1% TFA+64% acetonitrile and the objective MP47C peptide was eluted with 200 ml of 0.1% TFA+40% acetonitrile and recovered. The eluate was concentrated to 100 ml using an evaporator and lyophilized to provide 1.3 g of high-purity product.

(2) Epoxy-activation of a cellulose gel

To 90 ml of the applicant's prototype gel Kac, which is a cellulosic porous hard gel having an exclusion limit molecular weight of not less than $5\times10^6$ for globular proteins was added a sufficient amount of water to make 180 ml. Then, 60 ml of 2 M sodium hydroxide-water was added and the temperature was adjusted to 40° C. To this solution was added 21 ml of epichlorohydrin and the reaction was conducted at 40° C. with stirring for 1 hour. After completion of the reaction, the reaction product was thoroughly washed with water to provide an epoxy-activated cellulose gel.

(3) Immobilization of MP47C peptide and quantitation of the immobilized peptide

In 0.5 ml of 0.05 M borate buffer (pH 10.0) were dissolved 10 mg of MP47C peptide and 50 μg of sodium hydrosulfite (Wako Pure Chemical Ind.), and the solution was readjusted to pH 10 and made up to 1.0 ml with 0.01 N sodium hydroxide-water. The MP47C solution (whole amount) was added to 1 ml of the above epoxy-activated cellulose gel, and after 16 hours of shaking at 37° C. (MP47C peptide-:sodium hydrosulfite=1:372, sodium hydrosulfite=0.58 mmol/L), the reaction mixture was washed with a sufficient amount of PBS (10 mM phosphate buffer containing 150 mM sodium chloride) to provide Kac-MP47C-a (8 mg/ml-gel). The amount of immobilized MP47C peptide was calculated from the ratio of areas before and after the reaction on HPLC. μ-bondasphere C18 (Nippon Waters, 3.9 mm ID×150 mm H) was used as the column and (A): 0.1% TFA/$H_2O$ and (B):80% acetonitrile/0.1% TFA/$H_2O$ were used as the mobile phase. Thus, elution was started at (A):(B)=95:5 and the proportion of (B) was increased on a gradient of 3%/min. The flow rate was 1 ml/min.

(4) Evaluation of the IgG-binding activity of Kac-MP47C-a

Kac-MP47C-a or the ligand-free support (Kac) (1 ml) was taken in a vial, and after addition of 6 ml of healthy human serum, the vial was shaken at 37t for 2 hours. Then, this suspension was centrifuged at 5000 rpm for 1 minute and the IgG concentration of the supernatant was determined by turbidimetric immunoassay with Shionogi Biolaboratories. The IgG adsorption rate was calculated by the following formula.

Adsorption rate (%)={(Ir–It)/Ir}×100

Ir: IgG concentration of Kac support supernatant

It: IgG concentration of Kac-MP47C-a adsorbent supernatant

As a result, the IgG adsorption rate of Kac-MP47C-a was found to be 61%.

EXAMPLE 4

Immobilization of a Portion (Fab) of Anti-IgG Antibody on Tresyl-activated Sepharose 4B (Sepharose 4B-Fab-a)

(1) Immobilization of a portion (Fab) of anti-IgG antibody on tresyl-activated Sepharose 4B and quantitation of immobilized Fab Using a small amount of 1 mM HCl-water, 4 g of tresyl-activated Sepahrose 4B (Amersham Pharmacia Biotech) was caused to swell for 15 minutes. The support was then washed 30 with 1 mM HCl-water and further with a coupling buffer (pH 8.0, 0.5 M NaCl–0.1 M NaHCO$_3$). In 2 ml of the coupling buffer, 2 mg of the Fab prepared by papain digestion (PIERCE, ImmunoPure Fab Preparation Kit) from anti-human IgG (Fab) antibody (Binding Site) and 4.2 μg of sodium hydrogensulfite were dissolved. To this solution was added 0.4 ml of the above washed gel, and the reaction was conducted at 25° C. for 4 hours. The reaction product was washed with coupling buffer, then a block buffer (pH 9, 1 M ethanolamine-0.5 M sodium chloride-0.1 M NaHCO$_3$) was added, and the reaction was conducted at room temperature for 2 hours (Fab: sodium hydrogensulfite=1:1, sodium hydrogensulfite=20 μmol/L). The reaction product was washed with two different buffers for aftertreatment (pH 4.0, 0.5 M sodium chloride-0.1 M acetic acid-sodium acetate buffer; pH 8.0, 0.5 M sodium chloride-0.1 M-Tris-HCl buffer) alternately 3 times each to provide Sepharose 4B-Fab-a (4.0 mg/ml-gel). The immobilization amount was calculated from the concentrations of the anti-IgG Fab in the supernatants before and after the reaction as determined with Micro BCAProtein Assay Reagent Kit (PIERCE).

(2) Evaluation of the IgG-binding activity of Sepharose 4B-Fab-a

Sepharose 4B-Fab-a or the ligand-free support (Sepharose 4B), 0.2 ml, was taken in a vial and after addition of 0.6 ml of healthy human serum, the vial was shaken at 37° C. for 2 hours. Then, this suspension was centrifuged at 5000 rpm for 1 minute and the IgG concentration of the supernatant was determined by turbidimetric immunoassay with Shionogi Biolaboratories. The IgG absorption rate was calculated by the following formula.

Adsorption rate (%)={(Ir–It)/Ir}×100

Ir: IgG concentration of Sepharose 4B support supernatant

It: IgG concentration of Sepharose 4B-Fab-a adsorbent supernatant

As a result, the IgG adsorption rate of Sepharose 4B-Fab-a was found to be 82%.

Comparative Example 1

Immobilization of Aminoethanethiol on Sephacryl S1000 and Quantitation of Immobilized Aminoethanethiol (Sephacryl S1000-AET-b)

Except that sodium sulfite was not used, the procedure of Example 1 was otherwise repeated to immobilize aminoethanethiol on Sephacryl S1000 and provide Sephacryl S1000-AET-b (0.13 mg/ml-gel).

Comparative Example 2

Immobilization of Cysteine on Tresyl-Toyopearl and Quantitation of Immobilized Cysteine (Toyopearl-Cys-b)

Except that sodium pyrosulfite was not used, the procedure of Example 2 was otherwise repeated to immobilize cysteine on tresyl-Toyopearl and provide Toyopearl-Cys-b (0.07 mg/ml-gel).

Comparative Example 3-1

Immobilization of an IgG-binding Peptide (MP47C) on a Porous Support (Kac) (Kac-MP47C-b)

(1) Immobilization of MP47C and quantitation of immobilized MP47C

Except that sodium hydrosulfite was not used, the procedure of Example 3 was otherwise repeated to immobilize MP47C on Kac and provide Kac-MP47C-b (5 mg/ml).

(2) Evaluation of the IgG-binding activity of Kac-MP47C-b

Except that Kac-MP47C-b was used in lieu of Kac-MP47C-a, the procedure described in Example 3 under "Evaluation of the IgG-binding activity of Kac-MP47C-a" was faithfully followed to evaluate the IgG-binding activity. As a result, the IgG-adsorption rate of Kac-MP47-b was found to be 38%.

Comparative Example 3-2

Immobilization of an IgG-binding Peptide (MP47C) on a Porous Support (Kac) (Kac-MP47C-c) and Evaluation of the IgG-binding Activity of Kac-MP47C-c (1) Immobilization of MP47C and quantitation of immobilized MP47C Except that the amount of MP47C was changed to 20 mg, the procedure of Comparative Example 3-1 was otherwise repeated to immobilize MP47C on Kac and provide Kac-MP47C-c (8 mg/ml).

(2) Evaluation of the IgG-binding activity of Kac-MP47C-c

Except that Kac-M47C-c was used in lieu of Kac-MP47C-a, the procedure described in Example 3 under "Evaluation of the IgG-binding activity of Kac-MP47C-a" was faithfully followed to evaluate the IgG-binding activity. As a result, the IgG adsorption rate of Kac-MP47C-c was found to be 47%.

Comparative Example 4-1

Immobilization of a Portion (Fab) of anti-IgG Antibody on Tresyl-activated Sepharose 4B (Sepharose 4B-Fab-b)

(1) Immobilization of Fab on tresyl-activated Sepharose 4B and quantitation of immobilized Fab Except that sodium hydrogensulfite was not used, the procedure of Example 4 was otherwise repeated to immobilize a portion (Fab) of anti-IgG antibody on Sepharose 4B and provide Sepharose 4B-Fab-b (2.5 mg/ml-gel).

(2) Evaluation of the IgG-binding activity of Sepharose 4B-Fab-b

Except that Sepharose 4B-Fab-b was used in lieu of Sepharose 4B-Fab-a, the procedure described in Example 4 under "Evaluation of the IgG-binding activity of Sepharose 4B-Fab-a" was faithfully followed to evaluate the IgG-binding activity. As a result, the IgG adsorption rate of Sepharose 4B-Fab-b was found to be 65%.

Comparative Example 4-2

Immobilization of a Portion (Fab) of anti-IgG Antibody on Tresyl-activated Sepharose 4B (Sepharose 4B-Fab-c)

(1) Immobilization of Fab on tresyl-activated Sepharose 4B and quantitation of immobilized Fab Except that the amount of Fab was changed to 3 mg, the procedure of Comparative Example 4-1 was otherwise repeated to immobilize a portion (Fab) of anti-IgG antibody on Sepharose 4B and provide Sepharose 4B-Fab-c (4.0 mg/ml-gel).

(2) Evaluation of the IgG-binding activity of Sepharose 4B-Fab-c

Except that Sepharose 4B-Fab-c was used in lieu of Sepharose 4B-Fab-a, the procedure described in Example 4 under "Evaluation of the IgG-binding activity of Sepharose 4B-Fab-a" was faithfully followed to evaluate the IgG-binding activity. As a result, the IgG adsorption rate of Sepharose 4B-Fab-c was found to be 72%.

The immobilization amounts and activities of SH group-containing compounds in the above-mentioned Examples and Comparative Examples are summarized in Table 1.

TABLE 1

| | Abbreviation | Immobilization amount (mg/mL-gel) | Activity (%) |
|---|---|---|---|
| Example 1 | Sephacryl-AET-a | 0.20 | — |
| Compar. Ex. 1 | Sephacryl-AET-b | 0.13 | — |
| Example 2 | Toyopearl-Cys-a | 0.11 | — |
| Compar. Ex. 2 | Toyopearl-Cys-b | 0.07 | — |
| Example 3 | Kac-MP47C-a | 8 | 61 |
| Compar. Ex. 3-1 | Kac-MP47C-b | 5 | 38 |
| Compar. Ex. 3-2 | Kac-MP47C-c | 8 | 47 |
| Example 4 | Sepharose4B-Fab-a | 4 | 82 |
| Compar. Ex. 4-1 | Sepharose4B-Fab-b | 2.5 | 65 |
| Compar. Ex. 4-2 | Sepharose4B-Fab-c | 4 | 72 |

It will be apparent from Table 1 that in the examples using the method for immobilization of the present invention, SH group-containing compounds could be immobilized on solvent-insoluble supports in good yields and the inherent activity of the SH group-containing compound could be well sustained.

Constituted as described above, the present invention provides a novel method for immobilization by which SH group-containing compounds can be immobilized on solvent-insoluble supports in good yields and with good retention of the inherent activities of such SH group-containing compounds.

What is claimed is:

1. A method for immobilizing an SH group-containing compound which comprises reacting a solvent-insoluble support with said compound in the presence of an antioxidant, wherein said antioxidant is at least one member selected from the group consisting of sodium pyrosulfite (sodium disulfite), sodium sulfite, sodium hydrogensulfite and sodium hydrosulfite.

2. The method for immobilization according to claim 1 wherein the solvent-insoluble support is a water-insoluble support.

3. The method for immobilization according to claim 1 wherein the SH group-containing compound has a molecular weight of not more than $3 \times 10^4$.

4. The method for immobilization according to claim 1 wherein the SH group-containing compound is at least one member selected from the group consisting of amino acid, peptide and protein.

5. The method for immobilization according to claim 1 wherein the molar concentration ratio of the antioxidant to the SH group-containing compound is 1000:1 to 1:1000.

6. The method for immobilization according to claim 1 wherein the molar concentration of the antioxidant is 1 μmol/L to 1 mol/L.

7. The method for immobilization according to claim 1 wherein the solvent-insoluble support has been activated by at least one functional group selected from the group consisting of glycidyl, imidocarbonato, tosyl, tresyl, carboxyl, amino, azido and hydroxyl.

8. The method for immobilization according to claim 7, wherein the solvent-insoluble support has been activated by glycidyl group and/or tresyl group.

* * * * *